US00PP30587P2

(12) United States Plant Patent
Egger

(10) Patent No.: US PP30,587 P2
(45) Date of Patent: Jun. 18, 2019

(54) ***SEDUM* PLANT NAMED 'TNSEDDM'**

(50) Latin Name: *Sedum (Hylotelephium) telephium*
Varietal Denomination: TNSEDDM

(71) Applicant: Terra Nova Nurseries, Inc., Candy, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,027

(22) Filed: Jan. 25, 2018

(51) Int. Cl.
*A01H 5/12* (2018.01)
*A01H 6/32* (2018.01)

(52) U.S. Cl.
USPC ..... Plt./479

(58) Field of Classification Search
USPC ..... Plt./479
CPC ... A01H 5/02; A01H 5/00; A01H 5/10; A01H 6/328; A01H 6/749; A01H 6/32
See application file for complete search history.

(56) References Cited

PUBLICATIONS

Upov Pluto Plant Variety Database Jan. 8, 2019, retrieved on Jan. 8, 2019, retrieved from the Internet at www3.wipo.int/pluto/user/en/index.jsp, one page. (Year: 2019).*

* cited by examiner

*Primary Examiner* — June Hwu
(74) *Attorney, Agent, or Firm* — Klarquist Sparkman, LLP

(57) ABSTRACT

A new and distinct hybrid of *Sedum* plant substantially as shown and described characterized by glossy, green to olive green leaves with red serrated leaf margins, showy red stems, strongly upright stems, a medium, clumping habit, and excellent vigor.

2 Drawing Sheets

Botanical denomination: *Sedum* (*Hylotelephium*) *telephium.*

Variety designation: 'TNSEDDM'.

BACKGROUND OF THE INVENTION

The present invention relates to a new and distinct cultivar of *Sedum* (*Hylotelephium*) and given the cultivar name of 'TNSEDDM'. *Sedum* is in the family Crassulaceae. *Sedum* 'TNSEDDM' originated from a planned cross for compact multicrowned *Sedum* using *Sedum* 424-8, as the seed parent, and *Sedum* 420-8, as the pollen parent. Both parents are unnamed proprietary, unpatented *Sedum telephium* seedlings.

The Trademark designation for this variety is Double Martini.

Compared to *Sedum telephium* 424-8, the seed parent, the new cultivar has olive green leaves with red stems rather than green leaves with pink stems.

Compared to *Sedum telephium* 420-8, the pollen parent, the new cultivar has olive green leaves with red stems with multiple crowns rather than dark red leaves and few crowns.

Compared to *Sedum* 'Rosetta', U.S. Plant Pat. No. 26,190, the new cultivar has glossy green to olive green leaves with red leaf margins and red stems rather than blue green leaves and green stems.

This new and unique *Sedum* is distinguished by:

1. glossy, green to olive green leaves with red serrated leaf margins,
2. showy red stems,
3. strongly upright stems,
4. a medium, clumping habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one and a half-year-old *Sedum* 'TNSEDDM' growing in full sun in the trial bed outside in early June in Canby, Oreg.

FIG. 2 shows a two-year-old plant in the trial field in late June in Canby, Oreg.

FIG. 3 shows a close-up of the flowers in August.

DETAILED PLANT DESCRIPTION

Figure 4:
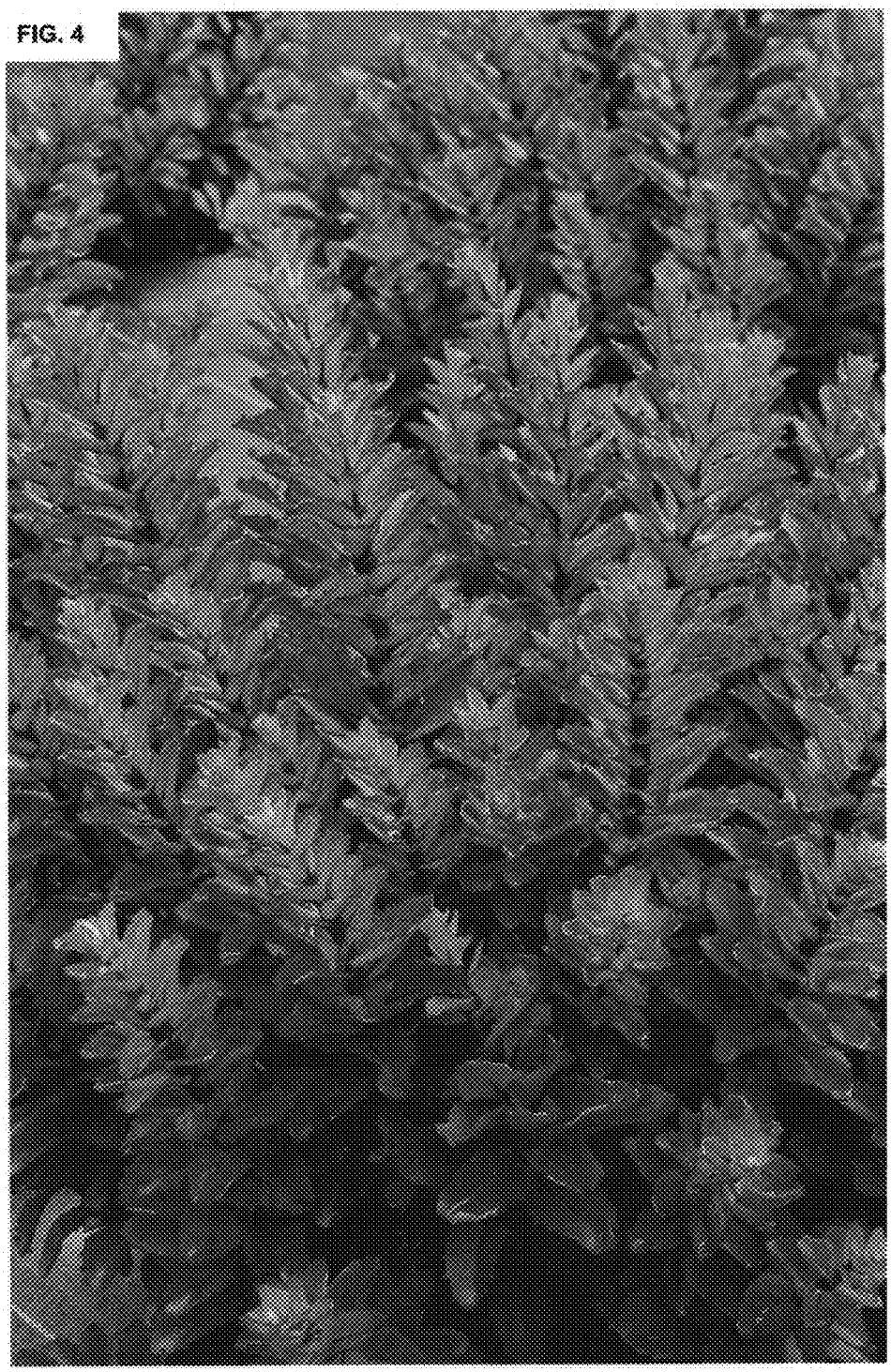
FIG. 4 shows a close-up of a two-year-old plant in the trial field in late June in Canby, Oreg.

The following is a detailed description of the new *Sedum* hybrid based on observations of three-year-old specimens grown in the trial bed in full sun under typical outdoor conditions in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The *Royal Horticultural Society Colour Chart,* 5th edition, 2007.

Plant:

*Type*.—Herbaceous perennial.

*Hardiness*.—USDA Zone 4 to 9.

*Size*.—45 cm tall from the ground to the top of the inflorescence and 50 cm wide.

*Habit*.—Erect, clumping.

*Vigor*.—Excellent.

Stem: Unbranched.

*Number*.—About 120.

*Size*.—Grows to 40 cm long and 7 mm wide.

*Internode length*.—2 mm to 20 mm.

*Surface*.—Glabrous, glossy.

*Color*.—Red 53A to Greyed Purple 187A over a base color of Yellow Green 146C.

Leaf:

*Type*.—Simple.

*Arrangement*.—Alternate.

*Shape*.—Oblong to elliptic to ovate.

*Apex*.—Acute.

*Base*.—Attenuate.

*Venation*.—Pinnate.

*Margins*.—Serrate to biserrate.

*Blade size*.—Grows to 4.5 cm long and 2.2 cm wide.

*Surface*.—Glabrous on both sides.

*Texture*.—Thick, succulent.

*Petiole*.—None, leaves sessile.

*Leaf color*.—Spring top and bottom side Yellow Green 147B with main vein Greyed Purple 187B on lower half of the leaf; summer topside Yellow Green 147B tinted Greyed Purple 187B under high sun intensity, with main vein Greyed Purple 187B on the lower half to ¾ of the leaf, margins often lightly tinted Greyed Purple 187A; bottom side Yellow Green 147B all over with main vein Greyed Purple 187B on bottom ½ to ¾ and margins 187A Inflorescence:

*Type*.—Terminal, corymbose, umbel-like.

*Number of flowers*.—About 600 per stem.

*Peduncle*.—None.

*Rachis*.—About 11 cm long and 6 mm wide, Greyed Purple 187A, succulent, glabrous.

*Pedicels*.—Grows to 3.5 mm long and 0.5 mm wide, glaucous, Brown 200B.

*Size*.—Grows to 13.5 cm long and 2.5 cm wide.

*Bloom period*.—August through September in Canby, Oreg.

Flower bud:

*Size*.—2.5 mm wide, 4 mm deep.

*Description*.—Conical.

*Color*.—Greyed Purple 187C on top quarter blending to 186C.

Flower:

*Type*.—Complete, actinomorphic.

*Shape*.—Stellate.

*Size*.—4.5 mm deep and 7 mm wide.

*Color*.—Greyed Purple 186B.

*Corolla description*.—4 mm deep and 7 mm wide, 5 petals, each lanceolate, cupped or reflexed, 4 mm long and 1.5 mm wide, margins entire, tip acuminate, base rounded, both sides glabrous and Red Purple 59A on top half and lightening to Red Purple 69B on bottom.

*Calyx description*.—1.5 mm deep and 3.5 mm wide, campanulate, 5 lobes, divided to the base, margins entire, tip acute, glabrous, Grey Brown N200A on both sides.

*Stamen description*.—8 in number, 4 mm long, filaments 4 mm long, Red Purple 64C, anthers 0.5 mm deep, shriveled, Black 203D, sterile, no pollen.

*Pistil description*.—5 separate prominent carpels, each 3 mm deep and 1.5 mm wide, Greyed Purple 186C on top half to Greyed Purple 186D on bottom half with stigma Greyed Purple 187A.

*Fragrance*.—None.

*Lastingness*.—Each stem lasts up to a month.

Fruit:

*Type*.—Ventrally dehiscent follicle, erect, attenuate.

*Fertility*.—None.

*Color*.—Brown 200A.

Seed: None seen.

Disease and pest resistance or tolerance: Pest and disease resistance are typical for this type of *Sedum*.

I claim:

1. A new and distinct hybrid of *Sedum* plant as herein illustrated and described.

* * * * *

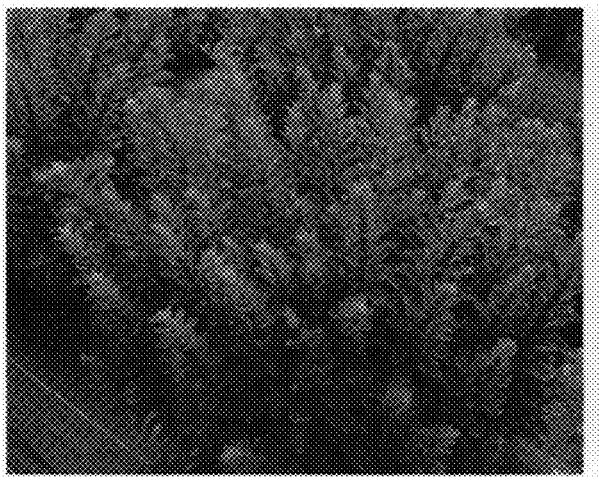
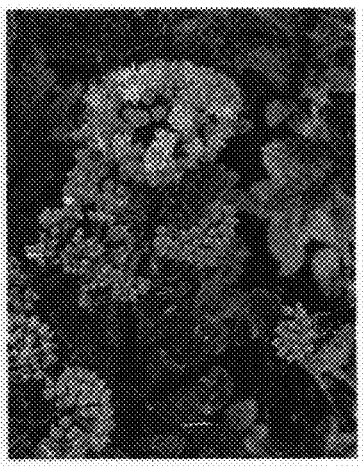

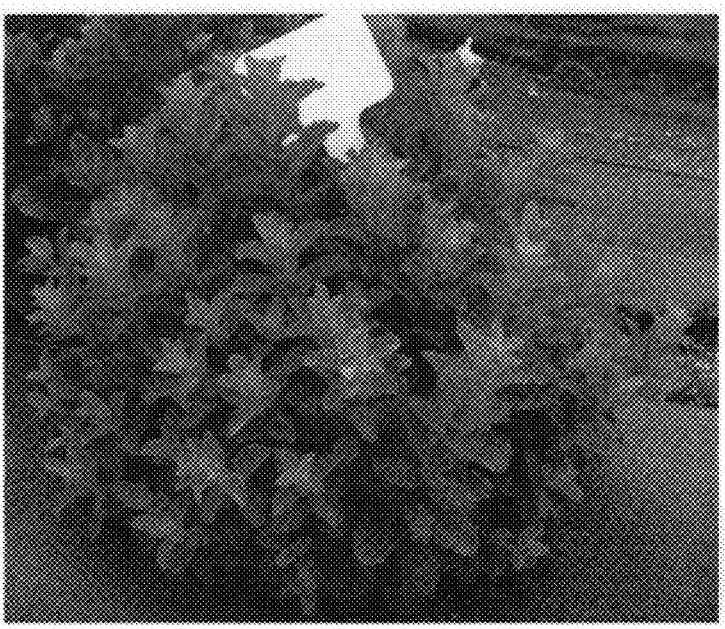
FIG. 1 on left,
FIG. 2 below left,
FIG. 3 below right